(12) United States Patent
Rakhyani et al.

(10) Patent No.: US 10,591,750 B2
(45) Date of Patent: Mar. 17, 2020

(54) DEVICE, SYSTEM AND METHOD FOR DETECTING A DIRECTION OF GAZE BASED ON A MAGNETIC FIELD INTERACTION

(71) Applicant: Verily Life Sciences LLC, Mountain View, CA (US)

(72) Inventors: Anil Kumar Ram Rakhyani, San Jose, CA (US); Stephen O'Driscoll, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 477 days.

(21) Appl. No.: 15/432,576

(22) Filed: Feb. 14, 2017

(65) Prior Publication Data

US 2017/0255026 A1    Sep. 7, 2017

Related U.S. Application Data

(60) Provisional application No. 62/303,311, filed on Mar. 3, 2016.

(51) Int. Cl.
*G02C 7/08* (2006.01)
*G02C 7/04* (2006.01)
(Continued)

(52) U.S. Cl.
CPC ............. *G02C 7/083* (2013.01); *A61B 3/113* (2013.01); *G01R 33/032* (2013.01); *G01R 33/07* (2013.01); *G02C 7/04* (2013.01); *A61F 2/1624* (2013.01)

(58) Field of Classification Search
CPC .......... G02C 7/02; G02C 7/028; G02C 7/101; G02C 7/04; G02C 7/61; G02C 7/083;
(Continued)

(56) References Cited

U.S. PATENT DOCUMENTS 6,730,123 B1    5/2004   Klopotek
2012/0140167 A1  6/2012   Blum
(Continued)

FOREIGN PATENT DOCUMENTS

EP          0162573      11/1985
WO      2008/101898 A1   8/2008
(Continued)

OTHER PUBLICATIONS

PCT/US2017/018406, International Search Report and Written Opinion of the International Searching Authority, dated May 30, 2017, 11 pages.
(Continued)

*Primary Examiner* — Collin X Beatty
*Assistant Examiner* — Grant A Gagnon
(74) *Attorney, Agent, or Firm* — Christensen O'Connor Johnson Kindness PLLC

(57) ABSTRACT

Techniques and mechanisms for determining a direction of gaze by a user of an ophthalmic device. In an embodiment, at least a portion of a magnetic field is generated by one of the ophthalmic device and an auxiliary reference device while the ophthalmic device is disposed in or on an eye of the user, and while the auxiliary reference device is adhered on the user's skin or under a surface of the skin. The ophthalmic device and the auxiliary reference device interact with each other via a magnetic field, and the interaction is detected with one or more sensors of the ophthalmic device. In another embodiment, the ophthalmic device stores predetermined reference information which corresponds various magnetic field signal characteristics each with a different respective direction of gaze. Based on the sensor information and the reference information, a controller of the ophthalmic device determines a direction in which the eye of the user is gazing.

22 Claims, 6 Drawing Sheets

(51) Int. Cl.
*A61F 2/16* (2006.01)
*A61B 3/113* (2006.01)
*G01R 33/07* (2006.01)
*G01R 33/032* (2006.01)

(58) Field of Classification Search
CPC .......... G02C 2202/20; G02C 2202/18; G02C 7/027; G02C 2202/16; G02C 2202/22; G02C 7/12; G02C 7/022; G02C 7/024; G02C 7/044; G02C 7/102; G02C 7/041; G02C 7/06; G02C 13/005; G02C 1/02; G02C 7/042; G02C 7/068; G02C 7/088; G02C 13/001; G02C 13/003; G02C 1/023; G02C 1/10; G02C 2202/10; G02C 2202/24; G02C 5/00; G02C 7/025; G02C 7/047; G02C 7/049; G02C 7/063; G02C 7/066; G02C 7/085; G02C 7/086; G02C 7/10; G02C 7/104; G02C 7/105; G02C 11/02; G02C 11/12; G02C 1/00; G02C 1/04; G02C 1/06; G02C 1/08; G02C 2200/02; G02C 2200/08; G02C 2202/02; G02C 2202/04; G02C 2202/08; G02C 2202/12; G02C 5/02; G02C 7/046; G02C 7/048; G02C 7/08; G02C 7/108; G02C 7/14; G02C 7/16; A61F 2/1618; A61F 2/16; A61F 2/1613; A61F 2/1637; A61F 2/164; A61F 2/1654; A61F 2230/0006; A61F 2/1645; A61F 2002/1699; A61F 2/1451; A61F 2/1616; A61F 2/1624; A61F 2/1632; A61F 2/1648; A61F 9/045; A61B 2034/104; A61B 34/10; A61B 3/032; A61B 3/0075; A61B 3/024; A61B 3/04; A61B 3/1005; A61B 3/13; A61B 5/107
USPC ......................................................... 351/159
See application file for complete search history.

(56) References Cited

U.S. PATENT DOCUMENTS

| | | |
|---|---|---|
| 2012/0206691 A1 | 8/2012 | Iwai |
| 2012/0245444 A1 | 9/2012 | Otis et al. |
| 2013/0218270 A1* | 8/2013 | Blanckaert .......... A61B 5/1107 623/6.17 |
| 2015/0025627 A1 | 1/2015 | Christie et al. |
| 2015/0305929 A1* | 10/2015 | Goldberg ............... G02B 1/043 604/521 |
| 2017/0188896 A1* | 7/2017 | Guth ...................... G02C 7/083 |

FOREIGN PATENT DOCUMENTS

| | | |
|---|---|---|
| WO | 2010/062504 A2 | 6/2010 |
| WO | 2014/194432 A1 | 12/2014 |
| WO | 2015/192080 A1 | 12/2015 |
| WO | 2017/015327 A1 | 1/2017 |

OTHER PUBLICATIONS

U.S. Appl. No. 14/831,671, filed Aug. 20, 2015, Hannaford et al.

* cited by examiner

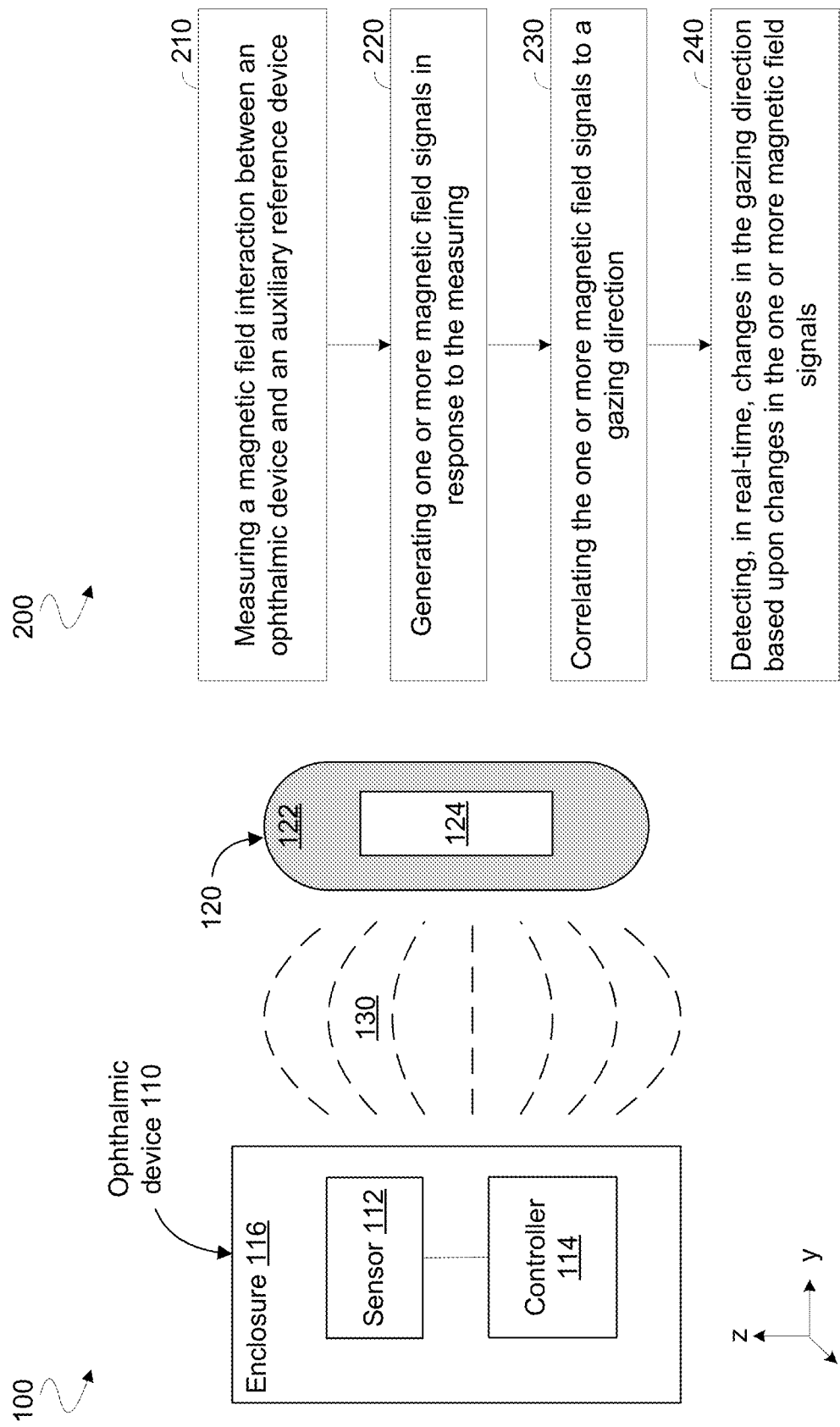

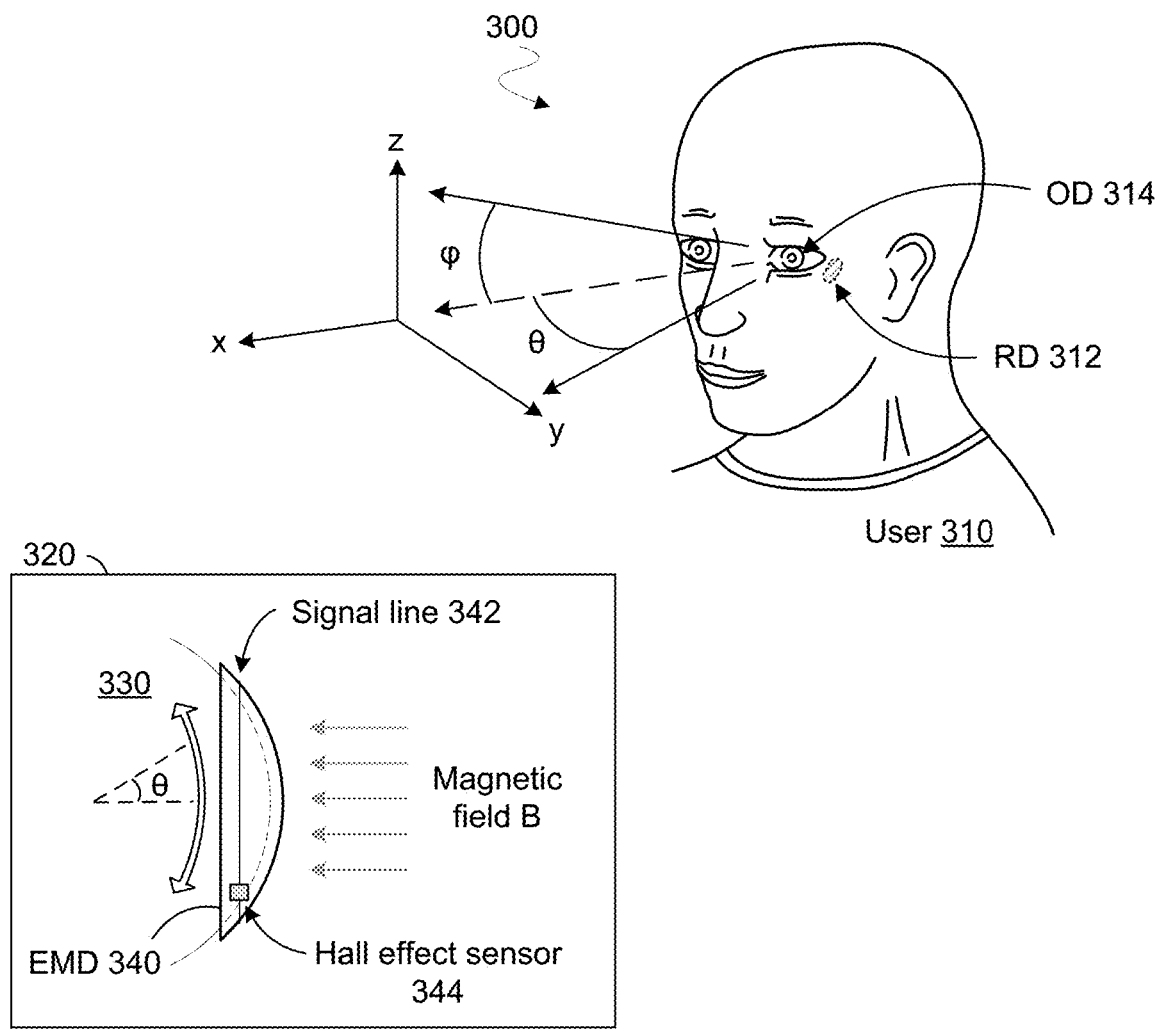
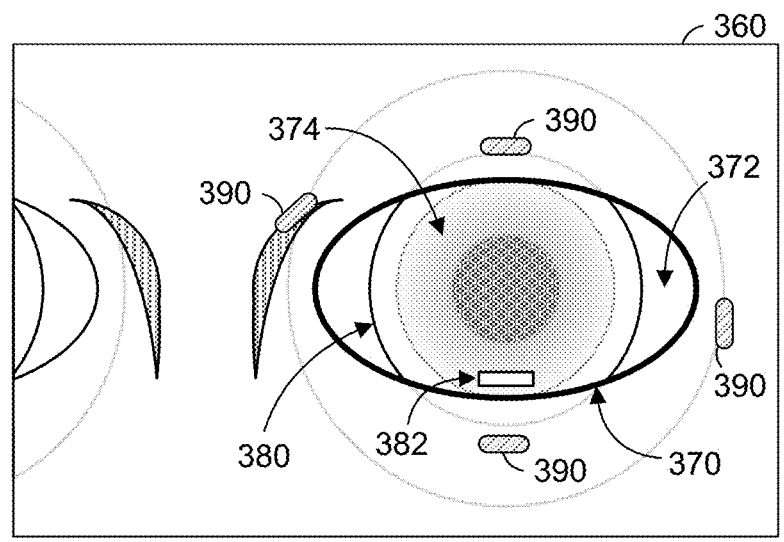
FIG. 3

DEVICE, SYSTEM AND METHOD FOR DETECTING A DIRECTION OF GAZE BASED ON A MAGNETIC FIELD INTERACTION

CROSS-REFERENCE TO RELATED APPLICATIONS

This application claims the benefit of U.S. Provisional Application No. 62/303,311, filed on Mar. 3, 2016, the entire contents of which are hereby incorporated by reference herein.

BACKGROUND

1. Technical Field

This disclosure relates generally to the field of optics, and in particular but not exclusively, relates to contact lenses.

2. Background Art

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages.

Recent technologies have begun to provide for various devices that operate in or on a human eye to aid the visual focus of a user. For some types of these devices, an accommodating lens includes one or more elements and circuitry to apply an electrical signal to change a focusing power of the one or more elements. Determining when to change such focusing power is often based on a direction of a gaze by a user of the optical device. As the capabilities of accommodation-capable optical devices continue to increase, there is expected to be an increased demand for such optical devices to provide accurate tracking of direction of gaze by a user.

BRIEF DESCRIPTION OF THE DRAWINGS

The various embodiments of the present invention are illustrated by way of example, and not by way of limitation, in the figures of the accompanying drawings and in which:

FIG. 1 is a functional block diagram illustrating elements of a system to determine a direction of gaze by a user of an ophthalmic device according to an embodiment.

FIG. 2 is a flow diagram illustrating elements of a method to determine a direction of gaze by a user of an ophthalmic device according to an embodiment.

FIG. 3 shows various views each of a respective system to determine a direction of gaze by a user of an ophthalmic device according to a corresponding embodiment.

DETAILED DESCRIPTION

Figure 4A:
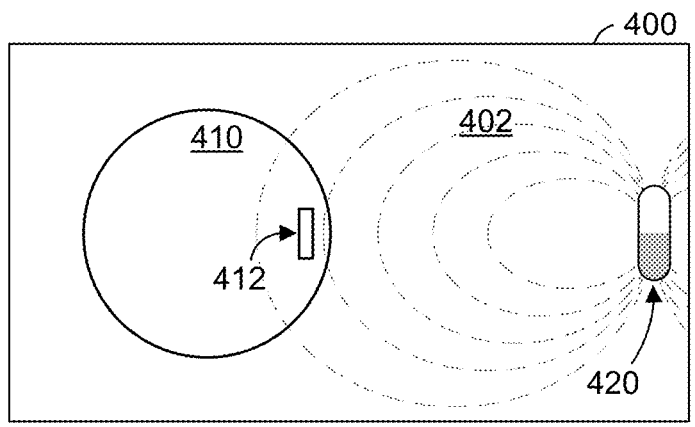
FIGS. 4A, 4B and 4C show elevation views each of a respective system to determine a direction of gaze by a user of an ophthalmic device according to a corresponding embodiment.

Embodiments described herein variously provide an apparatus, system and/or method for determining a direction of gaze by a user of an ophthalmic device. In the following description numerous specific details are set forth to provide a thorough understanding of the embodiments. One skilled in the relevant art will recognize, however, that the techniques described herein may be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Certain features of various embodiments are described herein with reference to mechanisms and techniques for determining a direction of gaze by a user of an eye-mountable device (EMD) that is mountable as a contact lens and that provides functionality to automatically provide any of various levels of accommodation. However, such discussion may be extended to additionally or alternatively apply to any of a various other types of ophthalmic device. For example, an ophthalmic device according to some embodiments may include an intraocular lens (IOL) that is implantable in an eye and/or may support other functionality in addition to (or instead of) automatic accommodation.

An accommodation-capable ophthalmic device may assist viewing by a user with a condition such as presbyopia or a cataract. An amount of accommodation to be provided by such an ophthalmic device may be determined based at least in part on a direction of gaze by the user of the ophthalmic device. For example, a higher level of accommodation may be needed when the direction of gaze (corresponding to the eye's orientation in the user's skull) is relatively high in the user's field of view. By contrast, a relatively low level of accommodation may be needed when the direction of gaze is lower in the user's field of view and/or is oriented more toward the nose bone of the skull.

In some embodiments, the direction of gaze is determined based on an interaction between the ophthalmic device and another device (referred to herein as an "auxiliary reference device") that is adhered on or implanted in the user. Such an auxiliary reference device may be fixed relative to the user's skull, and may move relative to the user's eye and relative to the ophthalmic device disposed in or on the eye. An auxiliary reference device according to one embodiment includes a mechanism, such as a magnet or a coil, that can generate, or otherwise affect the generation of, a magnetic field that is sensed by one or more magnetic sensors of the ophthalmic device. Interaction with the auxiliary reference device via the magnetic field may enable the ophthalmic device to detect a position and/or an orientation of the ophthalmic device relative to the auxiliary reference device (and thus, relative to the user's skull).

For example, the ophthalmic device may include or otherwise have access to pre-determined reference information that corresponds various characteristics of magnetic field signals (for brevity, 'magnetic field signal characteristics' herein) each with a respective state of the ophthalmic device and/or the auxiliary reference device. Such magnetic field signal characteristics may include characteristics of one or more signal to generate the magnetic field and/or characteristics of one or more signal generated based on the magnetic field. The ophthalmic device may access the reference information, based on output from a magnetic sensor of the ophthalmic device, to identify a position and/or orientation of the ophthalmic device relative to the auxiliary reference device. Based on the identified position and/or orientation, the ophthalmic device may control operation of an accommodation actuator and/or other mechanism.

FIG. 1 illustrates features of a system 100 to detect a direction of gaze according to an embodiment. System 100 includes devices that are each to be variously disposed in or on the body of a user, where interaction between such devices via one or more magnetic fields is to facilitate detection of a direction of gaze by that user. Unless otherwise indicated, "auxiliary reference device," "reference device," "reference unit" and similar terms refer to a mechanism, such as that of an auxiliary reference device 120 of system 100, that operates to interact with an ophthalmic device via a magnetic field, wherein a direction of gaze is determined based on such interaction. An auxiliary reference device external to the ophthalmic device, or a component thereof, may serve as a reference for detecting a direction of gaze—e.g., relative to some baseline gaze direction. An auxiliary reference device may comprise a magnetic source configured to be positioned on or under the user's skin—e.g., peripherally to an eye of the user. The auxiliary reference device may thus have a fixed position, relative to the skull of the user, at least during a period of time during which the user's eye moves (along with an ophthalmic device disposed therein or thereon) within an orbital socket of the skull. The position of the ophthalmic device relative to the auxiliary reference device may thus correspond to an orientation of the user's eye within the skull. This relative position (and/or a change in such a relative position) may provide a basis for determining a direction of gaze by the user.

In the illustrative embodiment shown, system 100 includes an ophthalmic device 110 that is (or is configured to be) disposed in or on a user's eye (not shown). For example, an enclosure 116 of device 110 may form a biocompatible exterior to accommodate such disposition in or on the eye. System 100 may further comprise one or more other devices—e.g., including the illustrative auxiliary reference device 120—each of which is (or is configured to be) disposed on or under the user's skin. Ophthalmic device 110 may include a contact lens, or an intraocular device, comprising integrated circuitry, encapsulated by enclosure 116, to facilitate detection of a direction of gaze. Such integrated circuitry may include one or more magnetic sensors (such as the illustrative sensor 112 shown) and a controller 114. Sensor 112 may operate to detect one or more characteristics of a magnetic field 130 between ophthalmic device 110 and auxiliary reference device 120 (e.g., where magnetic field 130 is concurrent with and overlaps one or more other magnetic fields). Alternatively or in addition, sensor 112 may sense one or more characteristics of signaling to generate at least a portion of magnetic field 130. Based on sensor information output by sensor 112, controller 114 may determine a direction of gaze by an eye in which or on which is disposed ophthalmic device 110.

For example, controller 114 may comprise logic (e.g., application-specific integrated circuitry, executable instructions and/or the like) that, when executed, causes the controller 114 to measure, with one or more magnetic sensors such as sensor 112, a magnetic field interaction between the ophthalmic device 110 and auxiliary reference device 120. Such measuring may include generating magnetic field 130 with an electromagnet circuit of ophthalmic device 110—e.g., wherein the magnetic field interaction is measured as a load on the electromagnet circuit. The one or more magnetic sensors may be operated by controller 114 to generate one or more magnetic field signals in response to such measuring of the magnetic field interaction. In some embodiments, controller 114 operates to monitor the one or more magnetic field signals and to correlate the one or more magnetic field signals to a gazing direction of ophthalmic device 110.

For example, controller 114 may include or otherwise have access to pre-determined reference information (not shown) that corresponds various sets of sensor information each with a different respective configuration of ophthalmic device 110 and auxiliary reference device 120 relative to each other. Some or all configurations may each include, for example, a respective distance between ophthalmic device 110 and auxiliary reference device 120 and/or a respective angular offset between ophthalmic device 110 and auxiliary reference device 120.

Controller 114 may include logic operable to output one or more signals—based, for example, on information from sensor 112 and predetermined reference information—identifying or otherwise indicating an angular offset of the gaze direction from some reference direction. Such one or more signals may indicate the direction of gaze by identifying a distance and/or an angular offset between respective components of ophthalmic device 110 and auxiliary reference device 120—e.g., with respect to the illustrative x, y, z coordinate system shown. In an embodiment, signaling output by controller 114 is used to control an automatic accommodation and/or some other functionality that is provided by ophthalmic device 110.

Auxiliary reference device 120 is one example of an embodiment that may be disposed on or under the skin of a user of ophthalmic device 110 (or of some other user of an ophthalmic device). By way of illustration and not limitation, auxiliary reference device 120 may include a capsule or an adhesive bandage. Interaction with ophthalmic device 110 via magnetic field 130 may occur while auxiliary reference device 120 is within 1 cm of a surface of the user's skin—e.g., while auxiliary reference device 120 is also in a fixed position relative to the user's skull. Auxiliary reference device 120 may be small enough and/or light enough to be imperceptible by the user of ophthalmic device 100. An overall weight of auxiliary reference device 120 may be equal to or less than 1 ounce, for example. Alternatively or in addition, a total volume of auxiliary reference device 120 may be equal to or less than 1 $cm^3$—e.g., where such a volume is equal to or less than 500 $mm^3$ and, in some embodiments, equal to or less than 250 $mm^3$. In some embodiments, auxiliary reference device 120 has a maximum width (e.g., a diameter) that is equal to or less than 2.5 cm—e.g., where the maximum width is equal to or less than 2.0 cm and, in some embodiments, equal to or less than 1 cm. Alternatively or in addition, a smallest side of auxiliary reference device 120 may have a length that is equal to or less than 5 mm—e.g., where the smallest side is equal to or less than 2 mm. In some embodiments, the smallest side is equal to or less than 1 mm (e.g., equal to or less than 500 um). Alternatively or in addition, a maximum cross-sectional area of auxiliary reference device 120 may be equal to or less than 4 cm$^2$, for example. Such a maximum cross-sectional area may be equal to or less than 3 cm$^2$ and, in some embodiments, equal to or less than 2 cm$^2$. However, such weights and dimensions of auxiliary reference device 120 are merely illustrative, and not limiting on other embodiments.

Auxiliary reference device 120 may omit some functionality that is provided by one or more other devices that are included in, or are to operate with, system 100. For example, in one embodiment, any user interface mechanism (e.g., including any display, any microphone and/or any speaker) of system 100 is provided by one or more devices other than auxiliary reference device 120. Alternatively or in addition, any optics of system 100 may be provide by one or more devices other than auxiliary reference device 120. In one embodiment, any communication between auxiliary reference device 120 and ophthalmic device 110 (or between auxiliary reference device 120 and any other device, for example) is only via wireless signaling.

The illustrated embodiment of auxiliary reference device 120 includes an enclosure 122 (or other housing structure) having disposed therein a mechanism, illustrated as reference unit 124, that is to serve as a reference for determining a relative position and/or a relative orientation of ophthalmic device 110. Enclosure 122 may be at least partially transparent to electromagnetic energy, thus allowing one or more components of reference unit 124 to generate or interact with at least some component of the magnetic field 130 that extends between ophthalmic device 110 and auxiliary reference device 120.

In one embodiment, enclosure 122 includes any of a variety of biocompatible materials that facilitate implantation (e.g., subcutaneous injection) of auxiliary reference device 120 within the body of a user of ophthalmic device 110. By way of illustration and not limitation, enclosure 122 may include any of various polyimide, parylene, silicone, ceramic and/or other materials adapted from conventional implantable medical device technologies. In another illustrative embodiment, auxiliary reference device 120 is to be disposed on a surface of the user's skin. For example, enclosure 122 may include a flexible material—such as a woven fabric, a plastic (such as polyethylene or polyurethane), latex or other such material—and a coating comprising an acrylate, resin or other such adhesive for applying auxiliary reference device 120 onto an exterior surface of the user's skin.

Reference unit 124 illustrates any of a variety of mechanisms to generate or to interact with at least a portion of magnetic field 130. For example, reference unit 124 may include a permanent magnet and/or an electromagnet circuit (e.g., including a solenoid) to generate at least a portion of magnetic field 130. In such an embodiment, sensor 112 may operate to detect a strength and/or a direction of such a portion of magnetic field 130. A permanent magnet of reference unit 124 may include, for example, Neodymium (Nd), samarium-cobalt (SmCo) and/or any of a variety of other materials adapted from conventional techniques for generating a magnetic field.

Alternatively or in addition, one or more components (not shown) of ophthalmic device 110 may instead, or also, generate at least part of magnetic field 130. For example, ophthalmic device 110 may itself include a permanent magnet and/or an electromagnet circuit. In such an embodiment, reference unit 124 may include a circuit structure (e.g., including an antenna) that interacts with one or more components of magnetic field 130 that are generated by ophthalmic device 110. Such interaction may include coupling whereby the circuit structure of reference unit 124 functions as a load on the generation of magnetic field components by ophthalmic device 110. By way of illustration and not limitation, reference unit 124 may include an antenna to couple with at least a portion of magnetic field 130, the antenna including a conductor forming a coil, helix, logarithmic spiral and/or any of various other shapes. Such a conductor may include a non-ferromagnetic metal forming a microcoil, or other such structure.

In some embodiments, such an antenna includes any of various short dipole antenna structures, near field antenna structures and/or the like. As used herein, "antenna" refers to any structure that can operate to perform one or both of radiating an electromagnetic field and coupling to an electromagnetic field. This includes, for example, any of a variety of structures that facilitate a reactive exchange of energy—e.g., in addition to, any exchange of energy by electromagnetic radiation.

Reference unit 124 may interact with magnetic field 130 using only one or more passive circuit structures. For example, circuit structures of reference unit 124 may omit any transistors or other active circuit elements. Such one or more passive circuit structures may be energized using only a power source that is external to auxiliary reference device 120 (e.g., where such a power source is a component of ophthalmic device 110). In other embodiments, reference unit 124 (or some other component of auxiliary reference device 120) includes integrated circuitry to facilitate interaction with ophthalmic device 110 via magnetic field 130. By way of illustration, such integrated circuitry may modulate the generation of, or an interaction with, some component of magnetic field 130. Alternatively or in addition, such integrated circuitry may facilitate wireless communication between auxiliary reference device 120 and ophthalmic device 110 (and/or some other device, not shown).

FIG. 2 illustrates elements of a method 200, according to an embodiment, to detect a direction of gaze by a user of an ophthalmic device. Method 200 may include operations performed with some or all components of system 100, for example. In one embodiment, method 200 is performed by a device having some or all of the features of ophthalmic device 110. To illustrate certain features of various embodiments, method 200 is described herein with reference to a system 300 that is shown in FIG. 3. However, such discussion may be extended to additionally or alternatively apply to any of a variety of other devices and/or systems of devices, according to different embodiments. Some or all of system 300 may, in various embodiments, provide functionality that is alternative to and/or in addition to that provided according to method 200.

In an embodiment, method 200 includes, at 210, measuring a magnetic field interaction between an ophthalmic device and an auxiliary reference device (e.g., between ophthalmic device 110 and auxiliary reference device 120). The magnetic field interaction may take place via a magnetic field, such as field 130, which extends outside of the ophthalmic device in a region between the ophthalmic device and the auxiliary reference device. The magnetic field interaction (and the measuring thereof at 210) may occur while the auxiliary reference device is adhered onto, or disposed under a surface of, the skin of a user—e.g., while the ophthalmic device is disposed in or on an eye of that user.

Method 200 may further comprise, at 220, generating one or more magnetic field signals in response to the measuring at 210. As used herein, 'magnetic field signal' refers to a signal—e.g., including a voltage signal or a current signal—which is generated based on a sensing of a magnetic field, wherein the signal specifies or otherwise indicates a characteristic of the magnetic field. One or more magnetic field signals may, for example, indicate any of a variety of combinations of one or more static conditions and/or one or more dynamic conditions including, but not limited to, a magnitude, direction, rate of change, modulation, etc. of a magnetic field.

In the illustrative embodiment of FIG. 3, system 300 includes an ophthalmic device OD 314 disposed in or on an eye of a user 310 using system 100. The other eye of user 310 may also have another ophthalmic device (not shown) disposed therein or thereon. OD 314 may provide functionality such as that of ophthalmic device 110 or any of various other ophthalmic devices described herein. For example, system 300 may further comprise an auxiliary reference device RD 312 that is configured to remain in a fixed orientation relative to the head of user 310—e.g., at least while user 310 is variously viewing in different directions with OD 314 at different times. During such viewing, one of RD 312 and OD 314 may generate at least part of a magnetic field that extends into some region including the other of RD 312 and OD 314. One or more magnetic sensors (not shown) of OD 314 may determine, based the magnetic field and/or signaling to create the magnetic field, a direction of gaze by the eye of user 310. For example, a magnet or a circuit structure of RD 312 may interact with ophthalmic device 312 via such a magnetic field while ophthalmic device 312 is disposed in or on the eye of user 310, and also while RD 312 is adhered onto, or disposed under a surface of, the skin of user 310. In one embodiment, RD 312 is configured to interact with ophthalmic device 312 while within 2 cm of the eye in which (or on which) is disposed ophthalmic device 312. For example, RD 312 may be within 1 cm of the eye during interaction of RD 312 with OD 314.

In one embodiment shown by the detail view in inset 320, an eye-mountable device EMD 340 (e.g., OD 314) is disposed on an eye 330. EMD 340 may be configured to interact with an auxiliary reference device (not shown) via a magnetic field B that is generated at least in part by the auxiliary reference device or by a component of EMD 340. In an example embodiment, an enclosure material of EMD 340 has formed therein a signal line 342 in which other circuitry (not shown) of ophthalmic device 342 is to drive a current. EMD 340 may further comprise one or more sensors to measure a current, voltage and/or other signal characteristic based on signal line 342 conducting the current within magnetic field B.

By way of illustration and not limitation, a current in signal line 342, in combination with magnetic field B, may results in a Hall effect sensor 344 of EMD 340 exhibiting a voltage difference—e.g., along a line of a direction that is orthogonal to a direction of the current in signal line 342. Sensor information generated with Hall effect sensor 344—such as the one or more magnetic field signals generated at 220—may indicate a direction, strength and/or any of various other characteristics of magnetic field B (e.g., including a change, rate of change, etc. of a characteristic). In some embodiments, the EMD 340 includes an accommodation actuator (not shown)—e.g., wherein signal line 342, an electromagnet circuit and/or other such magnetic sensor circuit structure forms one or more loop structures which extend around some or all of a periphery of the accommodation actuator.

Method 200 may further comprise, at 230, correlating the one or more magnetic field signals generated at 220 to a gazing direction. For example, the correlating at 230 may include accessing or otherwise determining reference information which corresponds various magnetic field signal characteristics each with a different respective direction of gaze. The reference information may be provided, for example, as an a priori input to the ophthalmic device prior to a sensing of a gaze direction with the ophthalmic device. In some embodiments, the determining at 210 includes performing a configuration operation to calibrate a gaze detection functionality.

The correlating at 230 may include generating, based on a characteristic of the one or more magnetic field signals and further based on predefined reference information, one or more signals describing a direction of gaze by a user of the ophthalmic device. For example, the correlating at 230 may include performing a search of the reference information to identify, from among different magnetic field signal characteristics (e.g., different sets of magnetic field signal characteristics), those one or more magnetic field signal characteristics that most closely match the one or more magnetic field signals generated at 220. The correlating at 230 may further comprise selecting the direction of gaze which is identified by the reference information as corresponding to the most closely matching one or more magnetic field signal characteristics. In the illustrative embodiment shown in inset 320, reference information (not shown) stored at EMD 340 may be searched or otherwise processed by evaluation logic a controller of EMD 340 to select, calculate or otherwise determine a direction of gaze that most closely corresponds to the or more characteristics of magnetic field B that are detected with Hall effect sensor 344.

In an embodiment, method 200 further comprises, at 240, detecting, in real-time, changes in the gazing direction based upon changes in the one or more magnetic field signals. For example, controller logic of the ophthalmic device may operate to monitor the one or more magnetic field signals over time. Such monitoring may include or otherwise be based on a measuring the magnetic field interaction as a load on an electromagnet circuit of the ophthalmic device. In such an embodiment, method 200 may comprise modulating the magnetic field to induce the load. For example, the ophthalmic device may deliver energy via the magnetic field to power a modulation of the magnetic field by circuitry of the auxiliary reference device.

Although some embodiments are not limited in this regard, method 200 may further comprise operations (not shown) to provide an accommodation level with the ophthalmic device based on the gazing direction. For example, such operations may include electrically manipulating an accommodation lens of the ophthalmic device to automatically change an optical power of the ophthalmic device in response to the detecting at 240. Such electrical manipulating may include one or more processes that, for example, are adapted from conventional techniques and/or mechanisms which identify one of a plurality of gazing directions as corresponding to a particular optical power to be provided with an accommodation lens. The particular details of such conventional techniques and mechanisms are not detailed herein to avoid obscuring features of various embodiments.

The correlating at 230 may include, or otherwise be based on, a calibration, training or other initial configuration process—e.g., to determine magnetic field signal characteristics that are to be variously associated each with one of a baseline (or reference) direction of gaze and various degrees and/or types of deviation from that baseline direction of gaze. Such a configuration process may further determine, for each of various gaze directions other than the baseline, a respective one or more magnetic field signal characteristics that are indicative of that corresponding gaze direction.

By way of example and not limitation, such a configuration process may include configuration hardware, software and/or other such logic—e.g., included in a laptop, mobile device, or other external hardware (not shown) that communicates wirelessly with OD 314—operating to display some sequence of visual targets to user 310 while OD 314 and RD 312 interact via a magnetic field. The configuration logic may prompt user 310—e.g., through visual and/or audio output—to variously view such targets at different times, where the targets each have a known position, distance (depth) from user 310 and/or the like. In response, user 310 may provide to the calibration logic input (e.g., via a microphone, handheld device or the like) variously indicating when such targets are being viewed. The calibration target may continuously move to different positions, where user 310 indicates by a button press, verbal and/or other means when they are or are not visually tracking the moving target.

In some embodiments, two (or more) auxiliary reference devices may be arranged in a configuration that is fixed, relative to the skull of a user, and that enables such auxiliary reference devices to participate in different respective magnetic interactions with the same ophthalmic device. One or more magnetic sensors of the ophthalmic device may variously detect signal characteristics that are variously based each on a respective one of such interactions. A controller of the ophthalmic device may process the output of the one or more magnetic sensors, wherein the two or more auxiliary reference devices are used as multiple references for detecting a relative position of the ophthalmic device (and a corresponding direction of gaze by a user of the ophthalmic device).

For example, method 200 may further comprise the ophthalmic device measuring, with one or more magnetic sensors, a second magnetic field interaction between the ophthalmic device and a second auxiliary reference device which is also external to the ophthalmic device. The one or more magnetic sensors may further generate a second one or more magnetic field signals based on the second magnetic field interaction. In such an embodiment, the correlating at 230 may include correlating a combination of both the one or more magnetic field signals (generated at 220) and the second one or more magnetic field signals to the gazing direction.

By way of illustration and not limitation, as shown in inset 360 of FIG. 3, one embodiment may include an ophthalmic device 380 configured to be disposed in or on an eye 372—e.g., where ophthalmic device 380 is a contact lens to cover some or all of an iris 374 of eye 372 and that may be partially overlapped by an eyelid 370. Inset 360 illustrates some examples of locations 390 (on or under a surface of the user's skin) where such one or more auxiliary reference devices—e.g., including RD 312—might be variously located. However, the one or more auxiliary reference devices may be located in more, fewer and/or different locations near (e.g., within 2 cm) of eye 372. A range of possible locations of ophthalmic device 380 during movement of eye 372 may allow for interaction between ophthalmic device 380 and one or more auxiliary reference devices that are each disposed on or under a surface of the skin of the user. In an embodiment, ophthalmic device 380 includes one or more magnetic sensors—e.g., including the illustrative magnetic sensor 382—to detect interactions between ophthalmic device 380 and multiple auxiliary reference devices variously disposed each at a different respective one of the locations 390.

In one embodiment, ophthalmic device 380 includes circuitry that operates to determine a correspondence of auxiliary reference devices each with a different respective magnetic field or magnetic field response. By way of illustration and not limitation, a memory (not shown) of ophthalmic device 380 may store additional reference information that defines resonant frequencies and/or other signal characteristics that are to variously serve as signatures each of a different respective auxiliary reference device. Such signatures may be used by a controller of the ophthalmic device to distinguish a magnetic field interaction involving one auxiliary reference device from another magnetic field interaction involving a different auxiliary reference device. In distinguishing such interactions from one another, ophthalmic device 380 may determine a direction of gaze by eye 372 by performing calculations to triangulate a position and/or an orientation of ophthalmic device 380 relative to multiple auxiliary reference devices.

FIG. 4A illustrates features of a system 400 to determine a direction of gaze according to an embodiment. System 400 may include features of system 100 and/or system 300, for example. In an embodiment, operation of system 400 is performed according to method 200. System 400 includes an ophthalmic device 410 and an auxiliary reference device 420 that are to interact with one another via a magnetic field 402. Based on such interaction, ophthalmic device 410 may determine a direction of gaze by a user of ophthalmic device 410.

In the illustrative embodiment of system 400, auxiliary reference device 420 generates some or all of magnetic field 402. For example, magnetic field 402 may include at least some non-varying component that is provide by a permanent magnet of auxiliary reference device 420. Alternatively or in addition, auxiliary reference device 420 may include an electromagnet circuit (e.g., comprising a solenoid) that operates to provide some or all of magnetic field 402. Such an electromagnet circuit may modulate one or more components of magnetic field 402—e.g., where such modulation is to serve as a signature for distinguishing auxiliary reference device 420 from one or both of a background magnetism of the surrounding environment and any magnetic field signature of some other device (not shown). Although some embodiments are not limited in this regard, operation of such an electromagnetic circuit may be powered by an energy harvesting antenna (not shown) of auxiliary reference device 420. Such an energy harvesting antenna may be powered, for example, by signals from ophthalmic device 410 or from some other device (not shown) that is included in or operates with system 400.

A magnetic sensor 412 of ophthalmic device 410 may provide to a controller (not shown) of ophthalmic device 410 sensor information indicating a direction, strength and/or other characteristic of field 402. For example, magnetic sensor 412 may include one or more Hall effect sensors, a magnetic coupling detector, a giant magnetoresistance (GMR) sensor and/or any of a variety of other mechanisms adapted from conventional techniques for detecting a characteristic of a magnetic field and/or characteristics of signaling to generate a magnetic field. The details of such conventional techniques are not limiting on some embodiments, and are not detailed herein to avoid obscuring features of various embodiments.

Figure 4B:
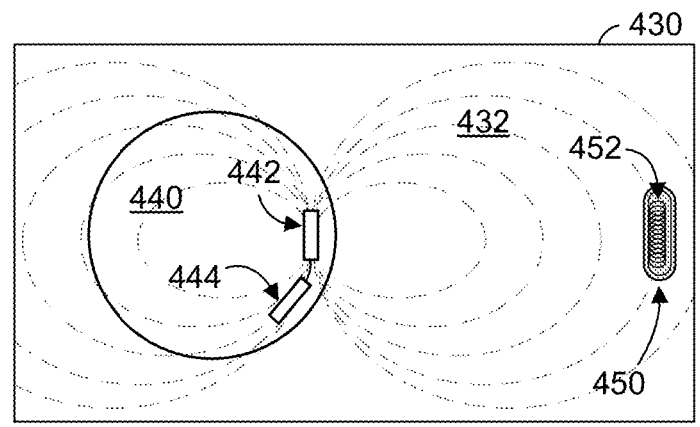

FIG. 4B illustrates another system 430 to determine a direction of gaze according to a different embodiment—e.g., where system 430 is an alternative embodiment to that of system 410. System 430 includes an ophthalmic device 440 and an auxiliary reference device 450 that are to interact with one another via a magnetic field 432. Based on such interaction, ophthalmic device 440 may determine a direction of gaze by a user of ophthalmic device 440. In the illustrative embodiment of system 430, a magnetic field generator 442 of ophthalmic device 440 provides some or all of magnetic field 402. For example, magnetic field generator 442 may include an electromagnet circuit. A passive circuit structure 452 of auxiliary reference device 450 may couple with magnetic field 402—e.g., the passive circuit structure 452 including an antenna structure such as a micro-coil. For example, auxiliary reference device 450 may interact with magnetic field 432 only via passive circuit elements, conductors and/or the like. Such coupling may serve as a load on an electromagnet circuit of magnetic field generator 442. The load may be detected with a magnetic sensor 444 of ophthalmic device 410, where such detection aids in determining a position of auxiliary reference device 450 relative to ophthalmic device 410.

Figure 4C:
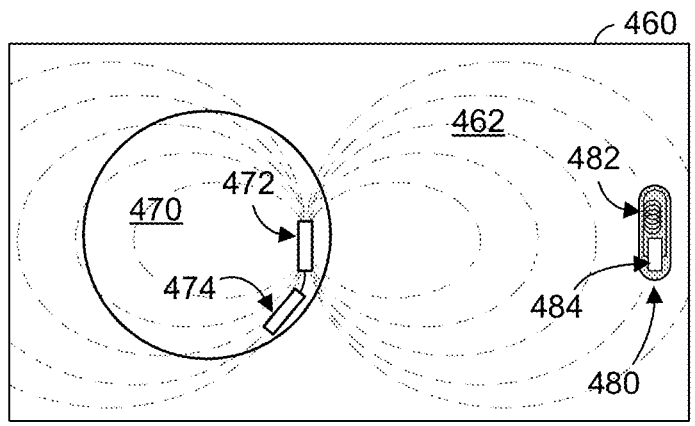

FIG. 4C illustrates a system 460 to determine a direction of gaze according to another embodiment—e.g., where system 460 is an alternative embodiment to one of systems 410, 430. System 460 includes an ophthalmic device 470 and an auxiliary reference device 480 that are to interact with one another via a magnetic field 462. Based on such interaction, ophthalmic device 470 may determine a direction of gaze by a user of ophthalmic device 470. In system 460, a magnetic field generator 472 of ophthalmic device 470 provides some or all of magnetic field 402. An antenna 482 of auxiliary reference device 480 may couple with magnetic field 402. Such coupling may be varied over time by a control circuit 480 of auxiliary reference device 480. For example, control circuit 480 may include integrated circuitry comprising active circuit elements that are powered by magnetic field 432 (and/or some other remote source of electromagnetic energy) to modulate coupling of antenna 482 with magnetic field 432. Such coupling may serve as a time-varying load on an electromagnet circuit of magnetic field generator 472, which may be detected with a magnetic sensor 474 of ophthalmic device 410. Such detection may in turn aid in a controller (not shown) of EMD 410 determining a position of auxiliary reference device 480 relative to EMD 410.

Figure 5:
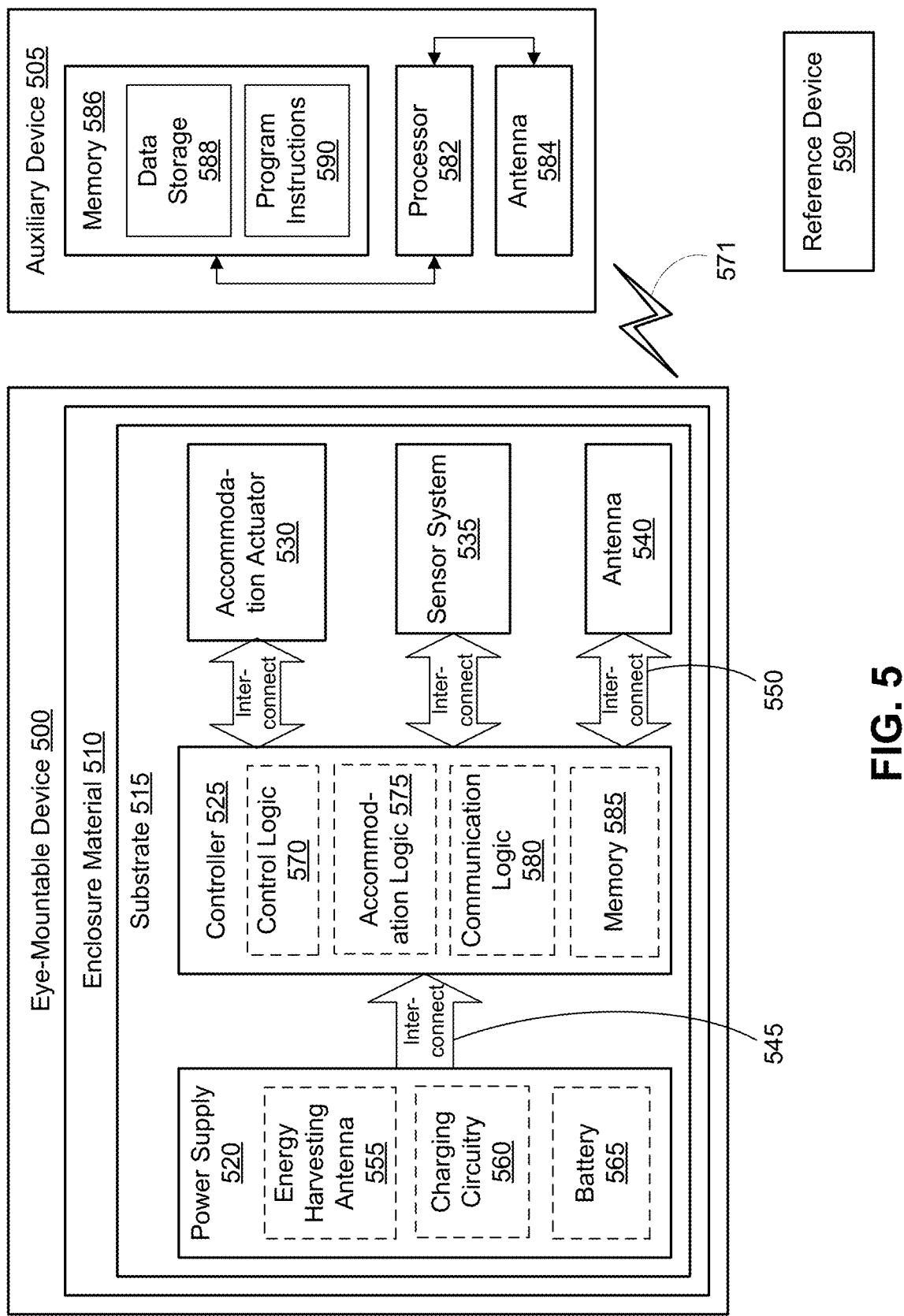
FIG. 5 is a functional block diagram of an ophthalmic device for auto-accommodation along with an external reader, in accordance with an embodiment of the disclosure.

FIG. 5 is a functional block diagram of an accommodation-capable eye-mountable device 500 to be accessed via an auxiliary device 505, in accordance with an embodiment. EMD 500 may include some or all features of one of ophthalmic devices 110, 314, 410, 430, 460, for example. An exposed portion of EMD 500 may include an enclosure material 510 formed to be contact-mounted to a corneal surface of an eye. A substrate 515 may be embedded within or surrounded by enclosure material 510 to provide a mounting surface for a power supply 520, a controller 525, an accommodation actuator 530, a sensor system 535, an antenna 540, and various interconnects 545 and 550. The illustrated embodiment of power supply 520 includes an energy harvesting antenna 555, charging circuitry 560, and a battery 565. The illustrated embodiment of controller 525 includes control logic 570, accommodation logic 575, and communication logic 580. The illustrated embodiment of auxiliary device 505 includes a processor 582, an antenna 584, and memory 586. The illustrated embodiment of memory 586 includes data storage 588 and program instructions 590.

Controller 525 may be coupled to receive feedback control signals from sensor system 535 and further coupled to operate accommodation actuator 530. Sensor system 535 may provide functionality such as that of one of sensors 112, 382, 412, 444, 474, for example. Power supply 520 supplies operating voltages to the controller 525 and/or the accommodation actuator 530. Antenna 540 may be operated by the controller 525 to communicate information to and/or from eye-mountable device 500. In one embodiment, antenna 540, controller 525, power supply 520, and sensor system 535 are all situated on the embedded substrate 515. In one embodiment, accommodation actuator 530 may be embedded within enclosure material 510, but is not disposed on substrate 515. Because eye-mountable device 500 includes electronics and is configured to be contact-mounted to an eye, it is also referred to herein as an ophthalmic electronics platform, contact lens, or smart contact lens.

To facilitate contact-mounting, the enclosure material 510 may have a concave surface configured to adhere ("mount") to a moistened corneal surface (e.g., by capillary forces with a tear film coating the corneal surface). Additionally or alternatively, the eye-mountable device 500 may be adhered by a vacuum force between the corneal surface and enclosure material 510 due to the concave curvature. While mounted with the concave surface against the eye, the outward-facing surface of the enclosure material 510 may have a convex curvature that is formed to not interfere with eye-lid motion while the eye-mountable device 500 is mounted to the eye. For example, the enclosure material 510 may be a substantially transparent curved disk shaped similarly to a contact lens.

Enclosure material 510 may include one or more biocompatible materials, such as those employed for use in contact lenses or other ophthalmic applications involving direct contact with the corneal surface. Enclosure material 510 may optionally be formed in part from such biocompatible materials or may include an outer coating with such biocompatible materials. Enclosure material 510 may include materials configured to moisturize the corneal surface, such as hydrogels and the like. In some instances, enclosure material 510 may be a deformable ("non-rigid") material to enhance wearer comfort. In some instances, enclosure material 510 may be shaped to provide a predetermined, vision-correcting optical power, such as can be provided by a contact lens. Enclosure material may be fabricated of various materials including a polymeric material, a hydrogel, PMMA, silicone based polymers (e.g., fluoro-silicon acrylate), or otherwise.

Substrate 515 includes one or more surfaces suitable for mounting the sensor system 535, controller 525, power supply 520, and antenna 540. Substrate 515 may be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) may be patterned on substrate 515 to form circuitry, electrodes, etc. For example, antenna 540 may be formed by depositing a pattern of gold or another conductive material on substrate 515. Similarly, interconnects 545 and 550 may be formed by depositing suitable patterns of conductive materials on substrate 515. A combination of resists, masks, and deposition techniques may be employed to pattern materials on substrate 515. Substrate 515 may be a relatively rigid material, such as polyethylene terephthalate ("PET") or another material sufficient to structurally support the circuitry and/or electronics within enclosure material 510. Eye-mountable device 500 may alternatively be arranged with a group of unconnected substrates rather than a single substrate. For example, controller 525 and power supply 520 may be mounted to one substrate, while antenna 540 and sensor system 535 are mounted to another substrate and the two may be electrically connected via interconnects.

In some embodiments, power supply 520 and controller 525 (and the substrate 515) may be positioned away from the center of eye-mountable device 500 and thereby avoid interference with light transmission to the eye through the center of eye-mountable device 510. In contrast, accommodation actuator 530 may be centrally positioned to apply optical accommodation to the light transmitted to the eye through the center of eye-mountable device 510. For example, where eye-mountable device 500 is shaped as a concave-curved disk, substrate 515 may be embedded around the periphery (e.g., near the outer circumference) of the disk. In some embodiments, sensor system 535 includes one or more discrete voltage and/or current sensors that are configured to detect one or more characteristics of a magnetic field (not shown) extending at least in part between EMD 500 and an auxiliary reference device 590 (e.g., one of devices 120, 312, 420, 450, 480). For example, sensor system 535 and auxiliary reference device 590 may include some or all of the respective features of sensor 112 and auxiliary reference device 120. Sensor system 535 and/or substrate 515 may be substantially transparent to incoming visible light to mitigate interference with light transmission to the eye.

Substrate 515 may be shaped as a flattened ring with a radial width dimension sufficient to provide a mounting platform for the embedded electronics components. Substrate 515 may have a thickness sufficiently small to allow the substrate to be embedded in enclosure material 510 without adversely influencing the profile of eye-mountable device 500. Substrate 515 may have a thickness sufficiently large to provide structural stability suitable for supporting the electronics mounted thereon. For example, substrate 515 may be shaped as a ring with a diameter of about 10 millimeters, a radial width of about 1 millimeter (e.g., an outer radius 1 millimeter larger than an inner radius), and a thickness of about 50 micrometers. Substrate 515 may optionally be aligned with the curvature of the eye-mounting surface of eye-mountable device 500 (e.g., convex surface). For example, substrate 515 may be shaped along the surface of an imaginary cone between two circular segments that define an inner radius and an outer radius. In such an example, the surface of substrate 515 along the surface of the imaginary cone defines an inclined surface that is approximately aligned with the curvature of the eye mounting surface at that radius.

In the illustrated embodiment, power supply 520 includes a battery 565 to power the various embedded electronics, including controller 525. Battery 565 may be inductively charged by charging circuitry 560 and energy harvesting antenna 555. In one embodiment, antenna 540 and energy harvesting antenna 555 are independent antennae, which serve their respective functions of energy harvesting and communications. In another embodiment, energy harvesting antenna 555 and antenna 540 are the same physical antenna that are time shared for their respective functions of inductive charging and wireless communications with auxiliary device 505. Additionally or alternatively, power supply 520 may include a solar cell ("photovoltaic cell") to capture energy from incoming ultraviolet, visible, and/or infrared radiation. Furthermore, an inertial power scavenging system may be included to capture energy from ambient vibrations.

Charging circuitry 560 may include a rectifier/regulator to condition the captured energy for charging battery 565 or directly power controller 525 without battery 565. Charging circuitry 560 may also include one or more energy storage devices to mitigate high frequency variations in energy harvesting antenna 555. For example, one or more energy storage devices (e.g., a capacitor, an inductor, etc.) may be connected to function as a low-pass filter.

Controller 525 contains logic to choreograph the operation of the other embedded components. Control logic 570 controls the general operation of eye-mountable device 500, including providing a logical user interface, power control functionality, etc. Accommodation logic 575 includes logic for monitoring feedback signals from sensor system 535, determining the current gaze direction or gaze distance of the user, and manipulating accommodation actuator 530 in response to provide the appropriate accommodation. The auto-accommodation may be implemented in real-time based upon feedback from the gaze tracking, or permit user control to select specific accommodation regimes (e.g., near-field accommodation for reading, far-field accommodation for regular activities, etc.). Circuitry of controller 525 may include or couple to a repository on substrate 515—as represented by the illustrative memory 585 (e.g., including volatile memory cells)—that, for example, is to store data written by such circuitry, data to determine operation of such circuitry and/or data received by (or to be sent from) EMD 500. Such a repository may store log information that describes performance of accommodation logic 575 and/or other components of controller 525.

Communication logic 580 provides communication protocols for wireless communication with auxiliary device 505 via antenna 540. In one embodiment, communication logic 580 provides backscatter communication via antenna 540 when in the presence of an electromagnetic field 571 output from auxiliary device 505. In one embodiment, communication logic 580 operates as a smart wireless radio-frequency identification ("RFID") tag that modulates the impedance of antenna 540 for backscatter wireless communications. The various logic modules of controller 525 may be implemented in software/firmware executed on a general purpose microprocessor, in hardware (e.g., application specific integrated circuit), or a combination of both.

Eye-mountable device 500 may include various other embedded electronics and logic modules. For example, a light source or pixel array may be included to provide visible feedback to the user. An accelerometer or gyroscope may be included to provide positional, rotational, directional or acceleration feedback information to controller 525.

It is noted that the block diagram shown in FIG. 5 is described in connection with functional modules for convenience in description, but does not necessarily connote physical organization. Rather, embodiments of eye-mountable device 500 may be arranged with one or more of the functional modules ("sub-systems") implemented in a single chip, multiple chips, in one or more integrated circuits, or otherwise.

Auxiliary device 505 includes an antenna 584 (or group of more than one antennae) to send and receive wireless signals 571 to and from eye-mountable device 500. Auxiliary device 505 also includes a computing system with a processor 582 in communication with a memory 586. Memory 586 may be a non-transitory computer-readable medium that may include, without limitation, magnetic disks, optical disks, organic memory, and/or any other volatile (e.g. RAM) or non-volatile (e.g. ROM) storage system readable by the processor 582. Memory 586 may include a data storage 588 to store indications of data, such as data logs (e.g., user logs), program settings (e.g., to adjust behavior of eye-mountable device 500 and/or auxiliary device 505), etc. Memory 586 may also include program instructions 590 for execution by processor 582 to cause the auxiliary device 505 to perform processes specified by the instructions 590. For example, program instructions 590 may cause auxiliary device 505 to provide a user interface that allows for retrieving information communicated from eye-mountable device 500 or allows transmitting information to eye-mountable device 500 to program or otherwise select operational modes of eye-mountable device 500. Auxiliary device 505 may also include one or more hardware components for operating antenna 584 to send and receive wireless signals 571 to and from one or both of eye-mountable device 500 and auxiliary reference device 590.

Auxiliary device 505 may be a smart phone, digital assistant, or other portable computing device with wireless connectivity sufficient to provide the wireless communication link 571. Auxiliary device 505 may also be implemented as an antenna module that may be plugged in to a portable computing device, such as in an example where the communication link 571 operates at carrier frequencies not commonly employed in portable computing devices. In some instances, auxiliary device 505 is a special-purpose device configured to be worn relatively near a wearer's eye to allow the wireless communication link 571 to operate with a low power budget. For example, the auxiliary device 505 may be integrated in a piece of jewelry such as a necklace, earing, etc. or integrated in an article of clothing worn near the head, such as a hat, headband, etc. In other embodiments, auxiliary device 505 is a personal computer or game console.

Figure 6A:
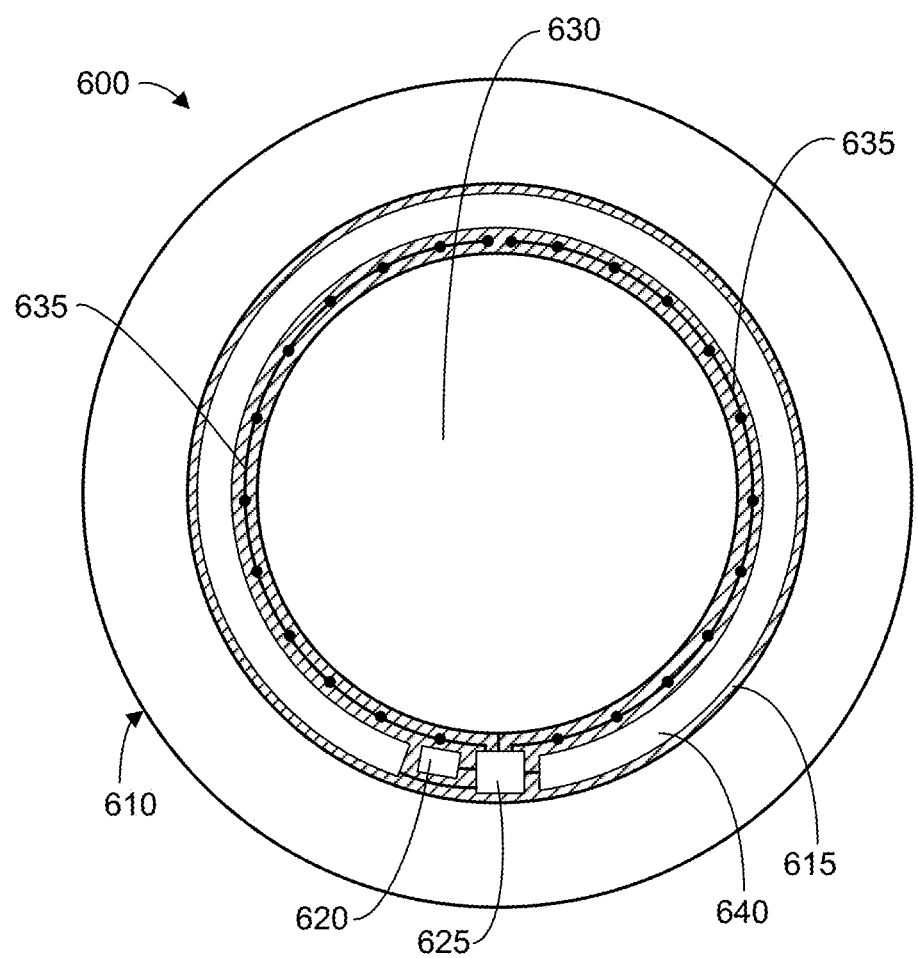
FIG. 6A is a top view of an ophthalmic device, in accordance with an embodiment of the disclosure.
Figure 6B:
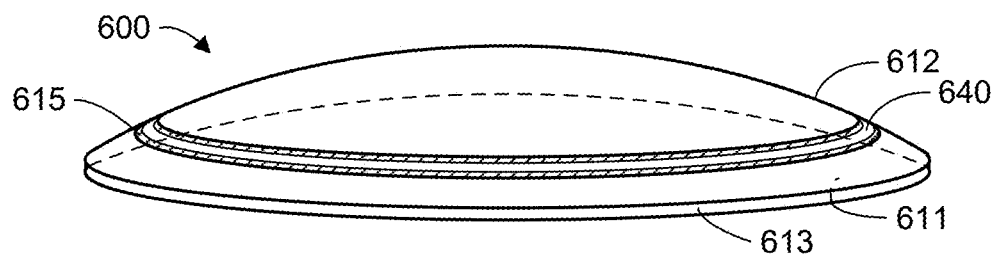
FIG. 6B is a perspective view of an ophthalmic device, in accordance with an embodiment of the disclosure.

FIGS. 6A and 6B illustrate two views of an eye-mountable device 600, in accordance with an embodiment of the disclosure. FIG. 6A is a top view of EMD 600 while FIG. 6B is a perspective view of the same. Eye-mountable device 600 is one possible implementation of eye-mountable device 500 illustrated in FIG. 5. The illustrated embodiment of eye-mountable device 600 includes an enclosure material 610, a substrate 615, a power supply 620, a controller 625, an accommodation actuator 630, a sensor system 635, and an antenna 640. It should be appreciated that FIGS. 6A and 6B are not necessarily drawn to scale, but have been illustrated for purposes of explanation only in describing the arrangement of the example eye-mountable device 600.

Enclosure material 610 of eye-mountable device 600 may be shaped as a curved disk. Enclosure material 610 is a substantially transparent material to allow incident light to be transmitted to the eye while eye-mountable device 600 is mounted to the eye. Enclosure material 610 may be a biocompatible material similar to those employed to form vision correction and/or cosmetic contact lenses in optometry, such as a polymeric material, polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate) combinations of these, or otherwise. Enclosure material 610 may be formed with one side having a concave surface 611 suitable to fit over a corneal surface of an eye. The opposite side of the disk may have a convex surface 612 that does not interfere with eyelid motion while eye-mountable device 600 is mounted to the eye. In the illustrated embodiment, a circular or oval outer side edge 613 connects the concave surface 611 and convex surface 612.

Eye-mountable device 600 may have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of eye-mountable device 600 may be selected according to the size and/or shape of the corneal surface of the wearer's eye. Enclosure material 610 may be formed with a curved shape in a variety of ways. For example, techniques similar to those employed to form vision-correction contact lenses, such as heat molding, injection molding, spin casting, etc. may be employed to form enclosure material 610.

Substrate 615 may be embedded within enclosure material 610. Substrate 615 may be embedded to be situated along the outer periphery of enclosure material 610, away from the central region where accommodation actuator 630 is positioned. In the illustrated embodiment, substrate 615 encircles accommodation actuator 630. Substrate 615 may not interfere with vision because it is too close to the eye to be in focus and is positioned away from the central region where incident light is transmitted to the light-sensing portions of the eye. In some embodiments, substrate 615 may optionally be formed of a transparent material to further mitigate effects on visual perception. Substrate 615 may be shaped as a flat, circular ring (e.g., a disk with a centered hole). The flat surface of substrate 615 (e.g., along the radial width) may be a platform for mounting electronics and for patterning conductive materials to form electrodes, antenna (e), and/or interconnections.

Sensor system 635 may be distributed about eye-mountable device 600 to sense one or more characteristics of a magnetic field between EMD 600 and an auxiliary reference device (not shown) that is remote from EMD 600. Such sensing may be used to determine a distance of the remote device from EMD 600 and/or a difference between respective orientations of EMD 600 and the remote device. By monitoring such magnetic field characteristics, feedback signals from sensor system 635 may be measured by controller 625 to determine the approximate gaze direction and/or focal distance. Sensor system 635 may be disposed within enclosure material 610 on substrate 615. In the illustrated embodiment, sensor system 635 is distributed peripherally around accommodation actuator 630 along the inner edge of substrate 615 between antenna 640 and accommodation actuator 630. In other embodiments, sensor system 635 may be alternatively distributed in or on eye-mountable device 600.

Accommodation actuator 630 may be centrally positioned within enclosure material 610 to affect the optical power of eye-mountable device 600 in the user's center of vision. In various embodiments, accommodation actuator 630 operates by changing its index of refraction under the influence of controller 625. By changing its refractive index, the net optical power of the curved surfaces of eye-mountable device 600 may be altered, thereby applying controllable accommodation. Accommodation actuator 630 may be implemented using a variety of different electro-active optical devices. For example, accommodation actuator 630 may be implemented using a layer of liquid crystal (e.g., a liquid crystal cell) disposed in the center of enclosure material 610.

In other embodiments, accommodation actuator 630 may be implemented using other types of electro-active optical materials such as electro-optic materials that vary refractive index in the presence of an applied electric field. Accommodation actuator 630 may be a distinct device embedded within enclosure material 610 (e.g., liquid crystal cell), or a bulk material having a controllable refractive index. In yet another embodiment, accommodation actuator 630 may be implemented using a deformable lens structure that changes shape under the influence of an electrical signal. Accordingly, the optical power of eye-mountable device 600 may be controlled by controller 625 with the application of electric signals via one or more electrodes extending from controller 625 to accommodation actuator 630.

Accommodation actuator 630 may be implemented using a variety of different liquid crystal structures including nematic liquid crystal, nematic twisted liquid crystal, cholesteric liquid crystal, or blue phase liquid crystal. Since a low switching voltage is desirable for low power chip design, nematic liquid crystals with switching voltages less than 5 V are suitable. With the application of a 5V control signal, refractive index switching ranging from approximately 1.74 in an off-mode to 1.52 in an on-mode is achievable. A refractive index shift of 0.2 should be sufficient to provide near-field accommodation for reading.

Returning to FIG. 6A, loop antenna 640 is a layer of conductive material patterned along the flat surface of the substrate to form a flat conductive ring. In some examples, to allow additional flexibility along the curvature of the enclosure material, loop antenna 640 may include multiple substantially concentric sections electrically joined together. Each section may then flex independently along the concave/convex curvature of eye-mountable device 600. In some examples, loop antenna 640 may be formed without making a complete loop. For instances, antenna 640 may have a cutout to allow room for controller 625 and power supply 620, as illustrated in FIG. 6A. However, loop antenna 640 may also be arranged as a continuous strip of conductive material that wraps entirely around the flat surface of substrate 615 one or more times. For example, a strip of conductive material with multiple windings may be patterned on the backside of substrate 615 opposite controller 625, power supply 620, and sensor system 635. Interconnects between the ends of such a wound antenna (e.g., the antenna leads) may then be passed through substrate 615 to controller 625.

Figure 7:
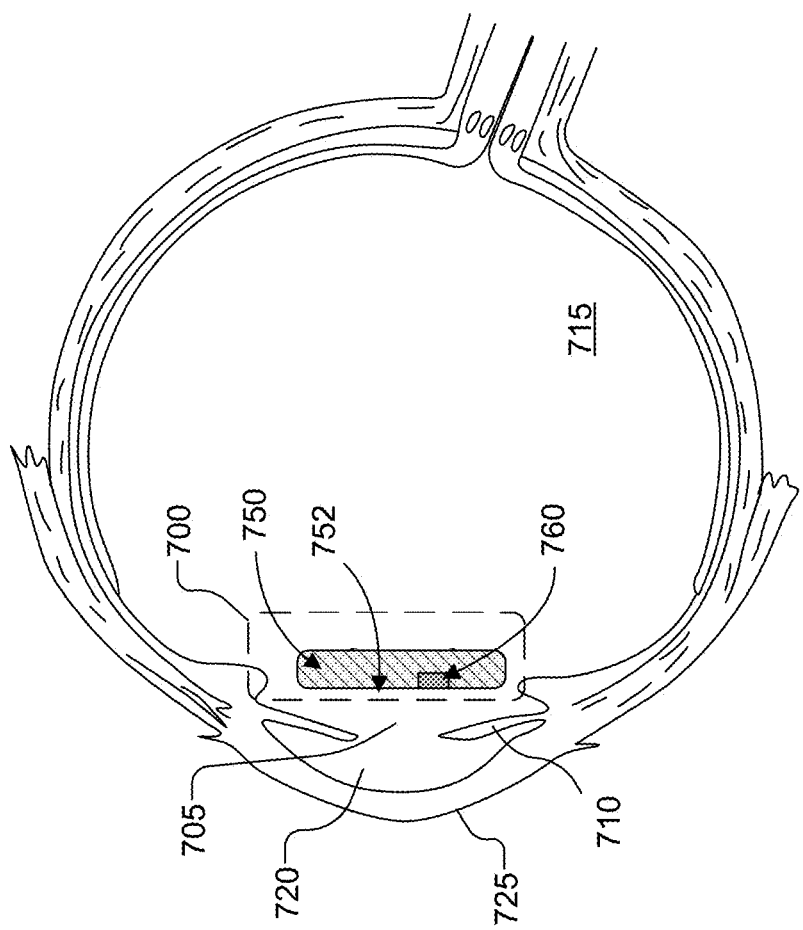
FIG. 7 is a cross-sectional illustration of an eye with an implanted intraocular device to detect gaze direction in accordance with one embodiment.

FIG. 7 is a cross-sectional illustration of an eye 715 having implanted therein an intraocular device 700 that, according to an embodiment, determines a direction of gaze based on an interaction, via a magnetic field, with an auxiliary reference device (not shown). Intraocular device 700 may include features of EMD 100 and/or features of one of ophthalmic devices 314, 410, 430, 460, 500, 600, for example.

The illustrated embodiment of intraocular device 700 includes a housing 750 and circuitry disposed therein. An exterior of intraocular device 700 may include a surface of housing 750 that is biocompatible to accommodate direct contact with an interior of a human (or other) eye. Such a surface of housing 750 may be formed by one or more materials that are both electromagnetically transparent (at least partially) and biocompatible to accommodate implantation of intraocular device 700. Examples of such materials include, but are not limited to, any of various biocompatible hydrogels, silicones, hydrophobic acrylics, fluorinated polymethacrylates and/or the like. In an embodiment, housing 750 includes a coating of biocompatible material that, for example, is formed by atomic layer deposition. Such materials may be adapted from those used in existing intraocular devices, for example.

Intraocular device 700 may be implanted into the anterior chamber, the posterior chamber, or other locations of a user's eye. Intraocular device 700 is illustrated as being implanted within the posterior chamber 705 behind an iris 710 of eye 715. However, intraocular device 700 may be implanted into other locations, as well, such as anterior chamber 720 disposed between iris 710 and cornea 725. In an embodiment, intraocular device 700 includes a housing 750 and circuitry 760 disposed in or on housing 750. Circuitry 760 may enable device 700 to interact via a magnetic field with an auxiliary reference device (not shown) that is in or on the body of the user of intraocular device 700. For example, circuitry 760 may be disposed at a side 752 of housing 750 that faces toward cornea 725—e.g., to sense a magnetic field (not shown) extending in posterior chamber 705. In an embodiment, circuitry 760 includes one or more magnetic sensors to detect one or more characteristics of such a magnetic field. Alternatively or in addition, such one or more magnetic sensors may detect a voltage and/or a current that is based on operation of other circuitry (included in or coupled to circuitry 760) that, for example, may generate at least part of such a magnetic field.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic system comprising:
  a magnetic field generator disposed within an enclosure of an ophthalmic device and configured to generate a magnetic field which extends beyond the ophthalmic device to interact with an auxiliary reference device external to the ophthalmic device;

a sensor disposed within the enclosure and coupled to the magnetic field generator to measure a magnetic field interaction with the auxiliary reference device as a load on the magnetic field generator, wherein the sensor is further configured to generate a magnetic field signal based on the magnetic field interaction;

an accommodation lens disposed within the enclosure; and a controller disposed within the enclosure and coupled to the sensor and the accommodation lens, wherein the controller includes logic that when executed by the controller causes the controller to perform operations including:

monitoring the magnetic field signal; and correlating the magnetic field signal to a gazing direction of the ophthalmic device.

2. The ophthalmic system of claim 1, wherein the controller includes further logic that when executed by the controller causes the controller to perform further operations including:

detecting, in real-time, changes in the gazing direction of the ophthalmic device based upon changes in the magnetic field signal; and electrically manipulating the accommodation lens to automatically change an optical power of the ophthalmic device in response to detecting changes in the magnetic field signal.

3. The ophthalmic system of claim 1, wherein the auxiliary reference device comprises a passive circuit that passively loads the magnetic field.

4. The ophthalmic system of claim 1, wherein the auxiliary reference device is configured to be implanted under a surface of skin of a user.

5. The ophthalmic system of claim 1, wherein the auxiliary reference device comprises an active circuit that is powered by the magnetic field from the ophthalmic device and presents a modulated load on the magnetic field.

6. The ophthalmic system of claim 1, wherein the controller further comprises logic that when executed by the controller causes the controller to perform further operations comprising:

modulating the magnetic field to induce the load on the magnetic field generator.

7. The ophthalmic system of claim 1, wherein the magnetic field generator comprises an electromagnet circuit including a conductor which extends around the accommodation lens.

8. An ophthalmic system comprising:

one or more magnetic sensors disposed within an enclosure of an ophthalmic device, the one or more magnetic sensors configured to measure magnetic field interactions with a plurality of auxiliary reference devices disposed external to the ophthalmic device, the one or more magnetic sensors further configured to generate magnetic field signals based on the magnetic field interactions;

an accommodation lens disposed within the enclosure; and a controller disposed within the enclosure and coupled to the magnetic sensors and the accommodation lens, wherein the controller includes logic that when executed by the controller causes the controller to perform operations including:

measuring, with the one or more magnetic sensors, the magnetic field interactions between the ophthalmic device and the auxiliary reference devices external to the ophthalmic device;

generating, with the one or more magnetic sensors, the magnetic field signals based on the magnetic field interactions; and correlating a combination of the magnetic field signals from the plurality of auxiliary reference devices to a gazing direction.

9. The ophthalmic system of claim 8, wherein measuring the magnetic field interactions includes:

detecting a first magnetic field modulation signature of a first one of the auxiliary reference device; and detecting a second magnetic field modulation signature of a second one of the auxiliary reference devices, wherein the first and second magnetic field modulations signatures enables the ophthalmic device to distinguish between the magnetic field interactions with the plurality of auxiliary reference devices for triangulation of a position or an orientation of the ophthalmic device relative to the plurality of auxiliary reference devices.

10. The ophthalmic system of claim 8, wherein the enclosure includes:

a concave surface; and a convex surface;

wherein the concave surface is configured to be removably mounted over a cornea and the convex surface is configured to be compatible with eyelid motion when the concave surface is so mounted.

11. The ophthalmic system of claim 8, wherein the ophthalmic device comprises an intraocular device.

12. The ophthalmic system of claim 8, wherein the magnetic sensors comprise Hall effect sensors.

13. A method at an ophthalmic device, the method comprising:

generating a first magnetic field with a magnetic field generator disposed in or on the ophthalmic device;

measuring a first magnetic field interaction between the ophthalmic device and a first auxiliary reference device external to the ophthalmic device as a load imparted by the first auxiliary reference device onto the magnetic field generator via the first magnetic field, the first magnetic field interaction occurring while the first auxiliary reference device is adhered on or disposed under a surface of skin of a user;

generating a first one or more magnetic field signals in response to the measuring the first magnetic field interaction;

correlating the first one or more magnetic field signals to a gazing direction of a cornea upon which the ophthalmic device is mounted or in which the ophthalmic device is disposed;

detecting, in real-time, changes in the gazing direction based upon changes in the first one or more magnetic field signals; and electrically manipulating an accommodation lens of the ophthalmic device to automatically change an optical power of the ophthalmic device in response to detecting changes in the gazing direction.

14. The method of claim 13, wherein the first auxiliary reference device comprises a passive circuit that passively loads the first magnetic field, the first auxiliary reference device positioned peripherally to an eye which includes the cornea.

15. The method of claim 13, wherein the ophthalmic device comprises an enclosure having a concave surface and a convex surface, wherein the concave surface is removably mounted over the cornea.

16. The method of claim 13, wherein measuring the first magnetic field interaction comprises measuring with one or more Hall effect sensors disposed within an enclosure of the ophthalmic device.

17. The method of claim 13, wherein the magnetic field generator comprises an electromagnet circuit of the ophthalmic device.

18. The method of claim 17, further comprising:

modulating the first magnetic field to induce the load on the electromagnet circuit.

19. The method of claim 17, wherein the electromagnet circuit comprises a conductor which extends around the accommodation lens.

20. The method of claim 17, wherein the generating the first magnetic field includes powering a modulation of the first magnetic field by the first auxiliary reference device.

21. The method of claim 13, further comprising:

measuring a second magnetic field interaction between the ophthalmic device and a second auxiliary reference device external to the ophthalmic device; and generating a second one or more magnetic field signals based on the second magnetic field interaction; wherein the correlating the first one or more magnetic field signals to the gazing direction includes correlating a combination of the first one or more magnetic field signals and the second one or more magnetic field signals to the gazing direction.

22. The method of claim 21, wherein measuring the first magnetic field interaction includes detecting a first magnetic field modulation signature of the first auxiliary reference device, and wherein measuring the second magnetic field interaction includes detecting a second magnetic field modulation signature of the second auxiliary reference device.

* * * * *